United States Patent [19]

Herzog et al.

[11] Patent Number: 5,311,633
[45] Date of Patent: May 17, 1994

[54] ELECTRIC POWER DRIVEN TOOTHBRUSH

[75] Inventors: Karl Herzog, Frankfurt am Main; Gustav Gassner, Kelkheim, both of Fed. Rep. of Germany

[73] Assignee: Braun Aktiengesellschaft, Frankfurt, Fed. Rep. of Germany

[21] Appl. No.: 854,670

[22] PCT Filed: Sep. 5, 1990

[86] PCT No.: PCT/DE90/00671
§ 371 Date: May 1, 1992
§ 102(e) Date: May 1, 1992

[87] PCT Pub. No.: WO91/07115
PCT Pub. Date: May 30, 1991

[30] Foreign Application Priority Data

Nov. 14, 1989 [DE] Fed. Rep. of Germany ....... 3937854

[51] Int. Cl.$^5$ .............................................. A46B 13/02
[52] U.S. Cl. ........................................ 15/28; 15/22.1; 74/25; 74/42; 433/131; 601/53
[58] Field of Search ............... 15/22.1, 28, 22.4, 22.2; 74/54, 25, 70, 75, 42; 128/45, 46, 48, 49; 433/118, 131

[56] References Cited

U.S. PATENT DOCUMENTS

| | | | |
|---|---|---|---|
| 1,212,440 | 1/1917 | Becker | 74/570 |
| 2,549,561 | 4/1951 | Baker | 74/42 |
| 2,844,965 | 7/1958 | Stelljes et al. | 74/70 |
| 3,046,584 | 7/1962 | Wepfer | 15/22.1 |
| 3,104,405 | 9/1963 | Perrinjaquet | 15/22.1 |
| 3,106,732 | 10/1963 | Dayton | 15/28 |
| 3,699,952 | 10/1972 | Waters et al. | 15/22.1 |
| 3,864,779 | 2/1975 | Thomas | 15/22.1 |
| 4,326,314 | 4/1982 | Moret et al. | 15/22.1 |
| 4,603,448 | 8/1986 | Middleton et al. | 15/22.1 |
| 4,756,202 | 7/1988 | Kawamoto | 15/22.1 |
| 5,054,149 | 10/1991 | Si-Hoe et al. | 15/28 |

FOREIGN PATENT DOCUMENTS

| | | | |
|---|---|---|---|
| 0110327 | 6/1984 | European Pat. Off. | |
| 0054043 | 11/1985 | European Pat. Off. | |
| 2002351 | 7/1970 | Fed. Rep. of Germany | 15/22.1 |
| 2368854 | 5/1978 | France | |
| 384539 | 2/1965 | Switzerland | |
| 369600 | 4/1932 | United Kingdom | |

OTHER PUBLICATIONS

Volmer, Getriebetechinik, pp. 136–139.

Primary Examiner—Stephen F. Gerrity
Assistant Examiner—Gary K. Graham
Attorney, Agent, or Firm—Fish & Richardson

[57] ABSTRACT

The invention is directed to an electric power driven toothbrush having a four-bar linkage (8) disposed in the handle section, the input end thereof being driven by an electric motor (2) through a train of spur gears, while the output end thereof drives in an oscillatory manner an output shaft (15) within an angular range of ±35°, approximately. The output shaft (15) is suitable for coupling engagement with a toothbrush section through a bevel gear train, and the axis of rotation of the toothbrush section forms an approximately right angle with the axis of the output shaft (15).

15 Claims, 2 Drawing Sheets

ELECTRIC POWER DRIVEN TOOTHBRUSH

BACKGROUND OF THE INVENTION

This invention relates to an electric power driven toothbrush with an electric motor disposed in a handle section and driving, through a driving mechanism and a translating device driven thereby, in an oscillatory manner a rotary toothbrush section, in which the driving mechanism is configured as a four-bar linkage including a crank adapted to be driven by means of the electric motor, the crank driving in an oscillatory manner at least indirectly a drive shaft of the toothbrush section by a means of a link and through a rocker.

A toothbrush of this type is already known from CH 384539 A. For one thing, however, the special configuration of the crank mechanism disclosed therein involves a large size which is undesirable in particular for toothbrushes. The crank is of the overhung type, that is, supported at only one end, involving an additional increase in size. For another thing, the crank bearing is subjected to major wear during operation of the toothbrush. Moreover, in this configuration of crank mechanism which is encapsulated in the housing to protect it from external influence, the problem exists of supplying the bearings with sufficient lubricating agents.

A further electric power driven toothbrush is known from EP 0 054 043 B1. Through an output shaft and a planetary gear train, the electric motor drives a toothbrush section drive shaft arranged in a sleeve-type shank. For this purpose, the drive shaft has at its output end an eccentrically disposed pin which is rotated by the drive shaft and is guided in a slotted guide of a drive member for the toothbrush section, the axis of which intersects angularly the axis of the drive shaft. The revolving motion of the pin causes rotation in alternating direction or oscillation of the drive member for the toothbrush section. Such a conversion of the rotary motion of the electric motor into an oscillating motion of the brush section allows, however, only a very small angle of rotation, because the slotted guide should be at a correspondingly large distance from the axis of the rotation of the toothbrush section for reducing the frictional resistances. The more closely the slotted guide approaches the axis of rotation of the toothbrush section, the higher become the frictional resistances, thus also increasing the noise developing in the operation of the toothbrush. The relatively large frictional resistance of the pin guided in the slotted guide also produces significant wear, resulting in a relatively short service life of the driving elements.

SUMMARY OF THE INVENTION

EP 0 110 327 A2 discloses an electric power driven toothbrush vibrating in oscillating fashion, in which the angle of oscillation is adjustable to various values. The toothbrush includes in particular a train of spur gears driven by the electric motor.

From U.S. Pat. No. 3,106,732 A a toothbrush becomes apparent having a rotary brush head arranged at right angles to the longitudinal axis of the toothbrush and rotatable by means of an angular driving mechanism.

GB 369 600 A discloses a toothbrush whose rotary brush head is arranged at right angles to the brush longitudinal axis of the toothbrush, the brush portion being a push fit on an output shaft and suitable for coupling engagement therewith.

FR 2 368 854 A discloses an electric power driven toothbrush vibrating in oscillating fashion, the oscillation assuming values in the range of between 55 and 66 Hertz.

By contrast, it is an object of the present invention to maintain a space-saving arrangement of the four-bar linkage in the housing of the toothbrush and to prolong the service like of the four-bar linkage.

This object is accomplished in that the crank is configured as an eccentric disk and the link as a connecting rod, and that the connecting rod includes a bearing eye receiving the eccentric disk in a rotatable relationship thereto, the eccentric disk having extending therethrough a spindle rotatably carried in a bearing block and in a bearing plate. A space-saving arrangement of the four-bar linkage in the housing of the toothbrush is obtained in that the four-bar linkage includes a crank configured as an eccentric disk and adapted to be driven by means of the electric motor, the crank driving in an oscillatory manner a drive shaft of the toothbrush section by a means of a link configured as a connecting rod and through a rocker. A substantial advantage of this eccentric disk is that the drive shaft rests in two bearings and is not of the overhung type. Because the connecting rod has a bearing eye rotatably receiving the eccentric disk fixedly connected to a spindle, the overall height of the driving mechanism is reduced and good adherence of the lubricating agents to the bearing points is ensured. In this arrangement, it is advantageous to provide on the spindle a train of spur gears or step gears in driving engagement with the eccentric disk and driven by the electric motor. This affords an economical way of reducing the relatively high rotational speed of the electric motor to the desired output speed, causing the toothbrush section to oscillate at the desired frequency.

A further advantage is that the drive shaft is in driving engagement with the toothbrush section through an angular driving mechanism. The use of an angular driving mechanism makes it possible to operate the toothbrush section at a low noise, its axis of rotation being disposed at approximately right angles to the axis of the drive shaft. In this arrangement, the angular driving mechanism is advantageously comprised of a bevel gear mounted on the drive shaft and a bevel gear connected to the toothbrush section, and is accommodated in a bevel gear casing arranged at the end of a sleeve-type shank.

The manipulation of the toothbrush section is facilitated in that the sleeve-type shank, in combination with the drive shaft and the bevel gear train, forms a subassembly which is adapted to be pushed onto an output shaft of the four-bar linkage for coupling engagement therewith.

Further, it is advantageous that the spindle for mounting the eccentric disk and an internal gear has its one end carried in a bearing block receiving the output shaft while its other end is carried in a bearing plate disposed in the housing and having extending therethrough the output shaft of the electric motor. This results in a highly compact and space-saving arrangement of the driving parts. To ensure that the user feels comfortable with the brush movement during the cleaning action when using a toothbrush rotating in alternating direction, that is, an oscillating toothbrush, the toothbrush section advantageously oscillates at a frequency of between 30 Hz and 60 Hz, preferably between 44 Hz and 50 Hz.

BRIEF DESCRIPTION OF THE DRAWINGS

Further advantages will become apparent from the subsequent description and the accompanying drawings illustrating a preferred embodiment of the invention. In the drawings.

DESCRIPTION OF THE PREFERRED EMBODIMENTS

Figure 1:
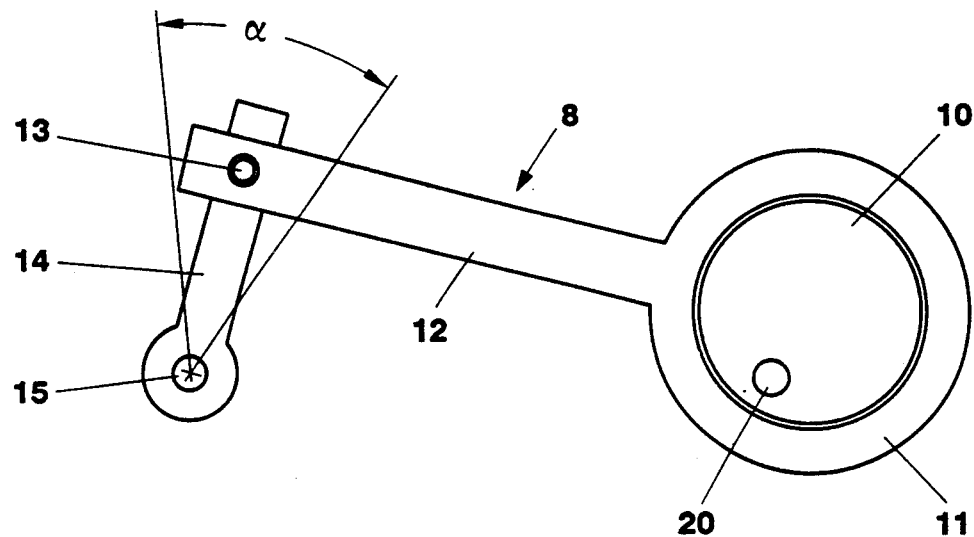
FIG. 1 is a schematic representation of the four-bar linkage for driving in an oscillatory manner a toothbrush section of an electrically powered toothbrush.
Figure 2:
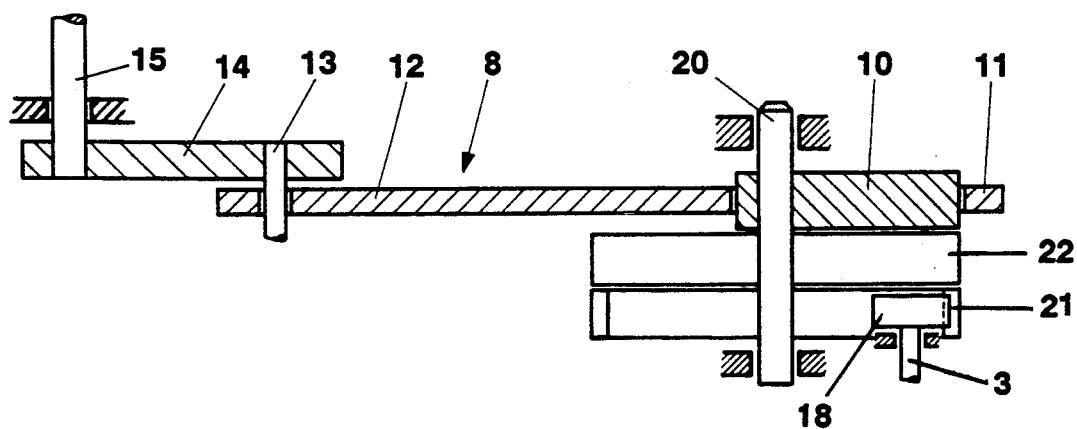
FIG. 2 is a longitudinal sectional view of the four-bar linkage of FIG. 1, projected into the plane of the drawing.

Referring now to the drawings, reference numeral 1 designates the forward end of an inner housing receivable in an outer housing not shown and configured as a handle. Seated in the bottom area of the inner housing 1 is an electric motor 2 having an output shaft 3 extending through a bearing plate 4 of a driving mechanism chamber 5 adjacent to the inner housing 1. A four-bar linkage 8 driven by the output shaft 3 is arranged in the mechanism chamber 5. The four-bar linkage 8 is comprised of a crank configured as an eccentric disk 10 and rotatably received in a bearing eye 11 of a connecting rod 12 configured as a link, its other end being pivotally connected to a rocker 14 by means of a pivot pin 13. As becomes apparent from FIGS. 1 and 2, the lower end of the rocker 14 is fixedly connected to an output shaft 15 rotatably received in a bearing block 16 connected to the mechanism chamber 5.

The output shaft 3 makes driving connection with a slip clutch 22 by means of a pinion 18 mounted on the output shaft and an internal gear 21 mounted on a spindle 20. The eccentric disk 10 received in the bearing eye 11 of the connecting rod 12 is flanged to or integrally formed on the output end 23 of the slip clutch 22. Extending through the eccentric disk 10 is the spindle 20 which in turn is passed through the bearing eye 11 of the connecting rod 12 and has its ends rotatably carried in the bearing block 16 and, respectively, the bearing plate 4.

Figure 3:
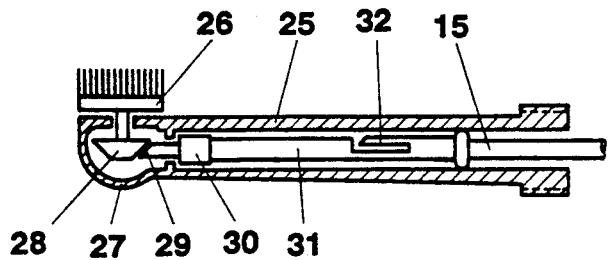
FIG. 3 is a view of the forward part of the electrically powered toothbrush, showing the sleeve-type shank for accommodating the drive shaft and the bevel gear train for driving the toothbrush body.
Figure 4:
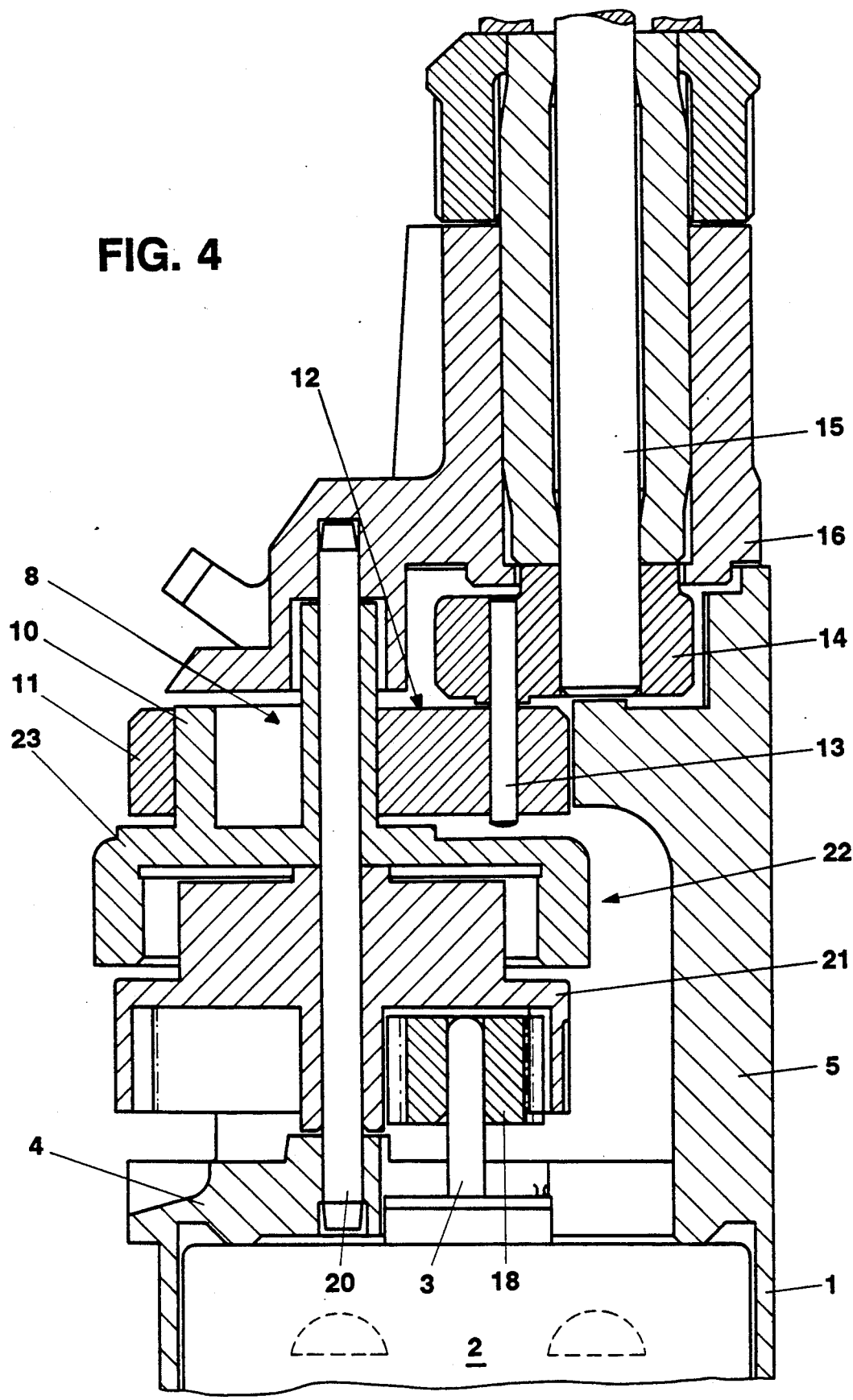
FIG. 4 is a view of the forward end of an electric motor mounted in the housing of the electrically powered toothbrush, showing the associated four-bar linkage and an output shaft suitable for coupling engagement with the drive shaft disposed in the sleeve-type shank.

The lower end of the rocker 14 is fixedly connected to the output shaft 15 which, as becomes apparent from FIG. 3, is insertable into a sleeve-type shank 25 for receiving a toothbrush section 26 in a rotatable relationship thereto.

The sleeve-type shank 25 has at its end a bevel gear casing 27 in which the toothbrush section 26 incorporating a bevel gear 28 is rotatably carried. The bevel gear 28 is in driving engagement with a further bevel gear 29 mounted on the forward end of a drive shaft 30 having a coupling sleeve 31 with a coupling bore suitable for insertion of the forward end of the output shaft 15. By inserting the output shaft 15 into the coupling bore, a rotary connection between the two shafts 15, 30 is established through a snap lock 32. To operate the toothbrush, the sleeve-type shank 25 is seated on the forward end of the outer housing configured as a handle in a manner preventing relative rotation, the shafts 15, 30 being coupled together in the process. After the sleeve-type shank 25 is coupled to the handle section, the electric motor 2 will drive the toothbrush section 26 through the four-bar linkage 8 at a frequency of between 2,400 and 3,000 strokes per minute, such that the rocker 14 oscillates within an angular range of ±35°, approximately. In an advantageous manner, the toothbrush section 26 is driven in alternating directions at a frequency of between 45 Hz and 50 Hz, approximately, imparting a pleasant cleaning sensation to the user and resulting in an optimum cleaning effect.

In lieu of the train of spur gears formed of internal gear 21 and pinion 18, a somewhat more costly planetary gear train may also be used. The use of the spur gear train in combination with the four-bar linkage 8 enables the motor power to be transmitted to the toothbrush section 26 with a small amount of wear, friction and noise at high rotational speeds.

Overall, examinations have revealed that a conversion of the rotary motion of the motor shaft into a rotary motion reversing direction in alternating sequence within a range of about ±35° of the toothbrush section 26 disposed angularly to the motor shaft by means of the four-bar linkage 8 described, in combination with the bevel gear train 28, 29, increases efficiency by as much as 100% as compared with the conventional conversion of motion according to the prior art initially described.

It will be understood that the four-bar linkage for producing an oscillatory rotating motion is not only suitable for use with toothbrushes in which the brush is mounted angularly to the longitudinal axis, but is also of great practical advantage in known toothbrush systems involving a conventional brush head vibrating vertically and/or horizontally (for example, Braun dental d3, Model No. 4804), in which the brush head may be preferably of a contour shaped in the manner of a circle or a circular segment.

We claim:

1. An elongated electric power driven toothbrush comprising a rotary toothbrush section coupled with an elongated drive shaft, said toothbrush further comprising a handle section, a driving mechanism, and an electric motor disposed in said handle section, wherein said driving mechanism comprises a crank, a connecting rod, and a rocker connected together as a four-bar linkage, said crank adapted to be driven by said electric motor said rocker being coupled to said drive shaft for oscillation therewith, said crank driving in an oscillatory manner at least indirectly said drive shaft of said toothbrush section through said connecting rod and said rocker, wherein said crank comprises an eccentric disk and said connecting rod includes a bearing eye receiving said eccentric disk in a rotatable relationship therethrough, said driving mechanism further comprising a spindle, a bearing block, and a bearing plate, said spindle extending through said eccentric disk and, on one side of said eccentric disk, being rotatably carried in said bearing block and, on an opposite side of said eccentric disk, being rotatably carried in said bearing plate.

2. The toothbrush as claimed in claim 1 wherein said toothbrush section is mounted for rotation about an axis that is disposed angularly to a longitudinal axis of said toothbrush.

3. The toothbrush as claimed in claim 2 wherein an axis of rotation of said rotary toothbrush section forms an angle of about 90° with said drive shaft.

4. The toothbrush as claimed in claim 1 further comprising a train of spur gears coupled to said spindle, said train of spur gears in driving engagement with said eccentric disk and driven by said electric motor.

5. The toothbrush as claimed in claim 4 wherein said train of spur gears comprises a pinion gear and an internal gear, said pinion gear mounted on an output shaft of said electric motor and making driving connection with said internal gear, which is mounted on said spindle.

6. The toothbrush as claimed in claim 5 wherein said bearing block receives said output shaft and said bearing plate is disposed in the housing and has extending therethrough the output shaft of said electric motor.

7. The toothbrush is claimed in claim 1 wherein said drive shaft is in driving engagement with said toothbrush section through an angular driving mechanism.

8. The toothbrush as claimed in claim 7 wherein said angular driving mechanism comprises a first bevel gear mounted on said drive shaft and a second bevel gear connected to said toothbrush section, an elongated sleeve-type shank extending from the handle section and rotatably supporting the drive shaft and a bevel gear casing coupled to the free end of the sleeve-type shank and housing said first and second bevel gears.

9. The toothbrush as claimed in claim 8 further comprising an output shaft connecting said rocker, and a wherein said sleeve-type shank in combination with said drive shaft toothbrush section, and said first and second bevel gears, forms a subassembly which is adapted to be pushed onto said output shaft for detachable coupling engagement therewith.

10. The toothbrush as claimed in claim 1 wherein the drive shaft of said toothbrush section oscillates at a frequency of between 30 Hz and 60 Hz.

11. An electric power driven toothbrush comprising a handle section, a rotary toothbrush section mounted for rotation and coupled with an elongated drive shaft, a driving mechanism, an electric motor disposed in said handle section and driving, through said driving mechanism in an oscillatory manner, said rotary toothbrush section at a frequency of between 30 Hz and 60 Hz, said driving mechanism comprises an eccentric disk, a connecting rod and a rocker connected together as a four-bar linkage assembly, said rocker being coupled to said drive shaft for oscillation therewith, said eccentric disk adapted to be driven by said electric motor, said eccentric disk driving in an oscillatory manner at least indirectly said drive shaft of said toothbrush section by a means of said connecting rod and rocker, said connecting rod including a bearing eye receiving said eccentric disk in a rotatable relationship, a spindle extending through said eccentric disk, a bearing block and a bearing plate located on opposite sides of said eccentric disk from each other and each rotatably carrying said spindle, a train of gears on said spindle in driving engagement with said eccentric disk, said train of gears comprising a pinion mounted on the output shaft of said electric motor and an internal gear on said spindle, an axis of rotation of said rotary toothbrush section forming an angle of about 90° with said drive shaft, and an angular driving mechanism for coupling said drive shaft in driving engagement with said toothbrush section.

12. The toothbrush as claimed in claim 11 and further including an elongated sleeve-type shank, extending from said handle section which in combination with said rotary toothbrush section and said drive shaft, forms a subassembly which is adapted to be pushed onto an output shaft of said four-bar linkage assembly for detachable coupling engagement therewith.

13. The toothbrush as claimed in claim 12 wherein said angular driving mechanism is comprised of a bevel gear mounted on said drive shaft and a bevel gear connected to said toothbrush section, said gears being accommodated in a bevel gear casing arranged at the free end of said sleeve-type shank.

14. The toothbrush as claimed in claim 11 wherein said bearing block receives said drive shaft and said bearing plate has extending therethrough the output shaft of said electric motor.

15. The toothbrush as claimed in claim 10, wherein the frequency is between 45 Hz and 50 Hz.

* * * * *